(12) United States Patent
Otto

(10) Patent No.: US 6,659,989 B1
(45) Date of Patent: Dec. 9, 2003

(54) CUTTING GUIDE FOR OSTOMY APPLIANCES

(75) Inventor: Jens Landkilde Otto, Copenhagen (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 09/806,493

(22) PCT Filed: Nov. 2, 1999

(86) PCT No.: PCT/DK99/00593

§ 371 (c)(1),
(2), (4) Date: Apr. 13, 2001

(87) PCT Pub. No.: WO00/25709

PCT Pub. Date: May 11, 2000

(30) Foreign Application Priority Data

Nov. 4, 1998 (DK) .......................... 1998 01423

(51) Int. Cl.[7] ................................. A61F 5/44
(52) U.S. Cl. .................... 604/344; 604/339; 604/342
(58) Field of Search ............... 604/336, 337, 604/338, 344, 339, 342

(56) References Cited

U.S. PATENT DOCUMENTS

| | | | |
|---|---|---|---|
| 3,419,006 A | 12/1968 | King | |
| 3,604,421 A | * 9/1971 | Pizzella | 604/335 |
| 3,646,936 A | * 3/1972 | Marsan | 604/344 |
| 3,837,342 A | * 9/1974 | Mitsuo | 128/DIG. 24 |
| 3,972,328 A | 8/1976 | Chen | |
| 4,252,120 A | * 2/1981 | Carpenter | 604/336 |
| 4,367,732 A | 1/1983 | Poulsen et al. | |
| 4,538,603 A | 9/1985 | Pawelchak et al. | |
| 4,552,138 A | 11/1985 | Hofeditz et al. | |
| 4,681,574 A | * 7/1987 | Eastman | 604/344 |
| 4,701,169 A | * 10/1987 | Steer | 604/338 |
| 4,867,748 A | 9/1989 | Samuelsen | |
| 4,894,058 A | * 1/1990 | Jensen | 604/332 |
| 5,051,259 A | 9/1991 | Olsen et al. | |
| 5,714,225 A | 2/1998 | Hansen et al. | |

FOREIGN PATENT DOCUMENTS

| | | | |
|---|---|---|---|
| DE | 4015186 A1 | * 11/1991 | ........... A61B/5/103 |
| EP | 0 264 299 | 4/1988 | |
| EP | 0 272 149 | 6/1988 | |
| EP | 0 415 183 | 3/1991 | |
| EP | 0 800 804 | 10/1997 | |
| GB | 1 280 631 | 7/1972 | |
| GB | 1570181 A | * 6/1980 | ............. A61F/5/44 |
| GB | 1 586 182 | 3/1981 | |
| WO | 88/06894 | 9/1988 | |
| WO | 98/17212 | 4/1998 | |

OTHER PUBLICATIONS

Two Piece Ostomy System Drainable Pouches, Hollister, 2 pgs.*
Marsan "Klear Seal" Adhesive Drains, No. 990, 1 pg.*

* cited by examiner

Primary Examiner—Karin Reichle
(74) Attorney, Agent, or Firm—Jacobson Holman PLLC

(57) ABSTRACT

A method for making a customized ostomy appliance including an adhesive wafer having the steps of measuring the outer periphery of the stoma of the patient, recording the information relating to the measurements of the stoma area, transforming the recorded information into electronic form, and utilizing the electronic information to select physical attributes of the ostomy device and have physical attributes selected in accordance with the measurement information transferred to the ostomy appliance. According to the method, the measurement information is utilized for printing a customized cutting guide pattern on a material for adhering to the adhesive wafer, offering a simple and efficient method of customizing ostomy appliances.

11 Claims, 3 Drawing Sheets

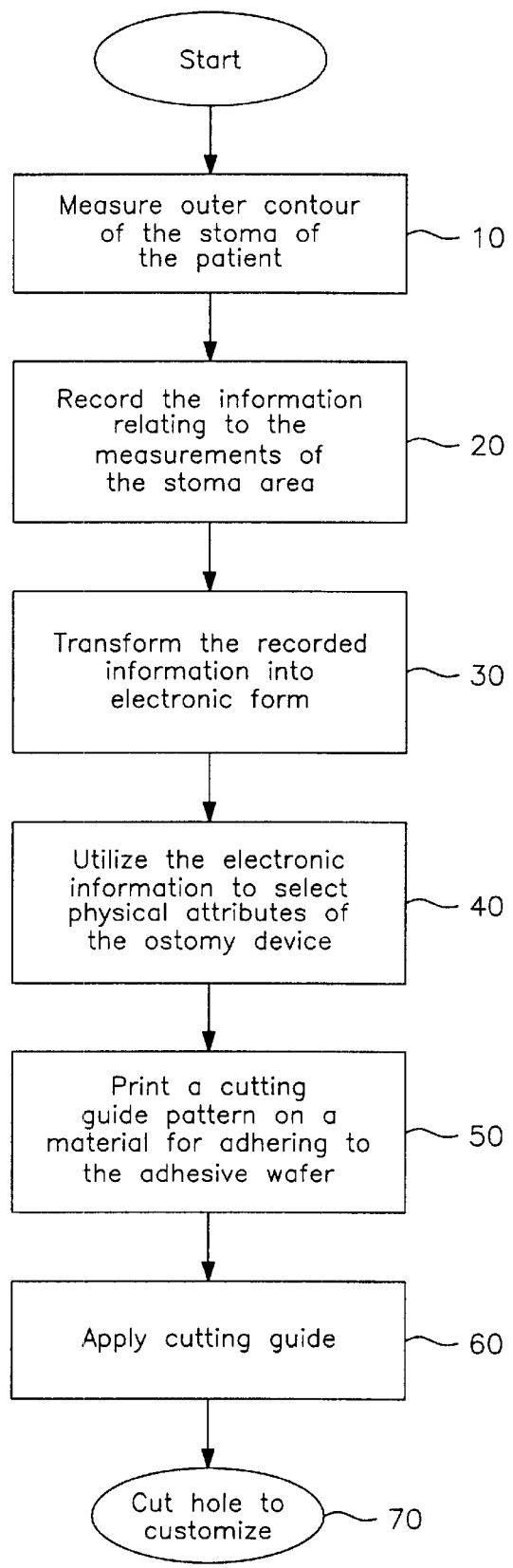

CUTTING GUIDE FOR OSTOMY APPLIANCES

BACKGROUND OF THE INVENTION

1. Field of the Invention

The present invention relates to a method for making customized ostomy devices of the type including a waste collection pouch adapted to be adhesively affixed to the skin surrounding the stoma and more particularly to cutting guides for ostomy devices customized to the stomal periphery of the user and a method for fabricating such cutting guides.

2. Description of the Related Art

In connection with surgery for a number of diseases in the gastro-intestinal tract a consequence is, in many cases, that the colon, the ileum or the urethra has been exposed surgically and the patient is left with an abdominal stoma and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma. Also in connection with a fistula, the patient will have to rely on an appliance to collect the bodily material emerging from such opening.

Ostomy appliances are well known. Such appliances may be two-piece or one-piece appliances. In both types of appliances, a body side member is attached to the wearer's abdomen, and optionally a receiving member or bag is attached to the body side ostomy member for receiving exudates from the ostomy in case of a two-piece appliance. The body side member comprises an adhesive wafer for securing the device to the wearer's abdomen, said wafer having a hole for accommodating the ostomy and conveying the material discharged through the artificial orifice or opening into the collection bag.

Wafers and ostomy devices are manufactured in a variety of different standard shapes, sizes and configurations to meet the many different needs of the users. Although these standard products meet the needs of the average user, they do not ideally meet the needs of any particular individual. In most cases, the user must adapt the product prior to use to suit his or her anatomy or lifestyle. Typical modifications which can be performed include cutting of the stoma receiving opening in the wafer, trimming the outside of the wafer, addition of convex inserts, application of paste and filters and folding or trimming the pouch. A conventional cutting guide is representatively depicted in FIG. 1.

However, even these modifications may not result in an ideal product for the particular individual. Users may have difficulty in performing the modifications, as well. This may be due to poor dexterity, poor eyesight or diminished mental capacity. Some desired modifications may be very difficult or impossible without special equipment. Some users may see making such modifications as taking too much time or for other reasons to be an undesirable task.

Thus, because of difficulties or simple reluctance on the part of the user, the modifications to the products are done poorly and as a result, product performance may suffer.

European patent publication No. EP 800 804 discloses the fabrication of customized ostomy devices according to which the ostomy devices are produced having attributes selected according to measurement information obtained from the respective patent.

This solution, however, involves substantial logistic problems with respect to producing, storing and distributing the customized products.

It is the general object of this invention to eliminate the above problems by fabricating ostomy devices which are customized so as to be uniquely suited to the needs and preferences of each individual user. This object may be achieved in a variety of different ways, using technologies of different sophistication and cost.

SUMMARY OF THE INVENTION

The present invention relates to a customized label having an adhesive backing for adhering to a release liner of an ostomy appliance having an adhesive wafer with a hole therein for adhering to the stomal area of a patient. The label includes a customized pattern defining a cutting line corresponding to the stomal area of the patient for adapting the opening to the patient's stoma. The pattern for the cutting line is obtained by measuring an outer contour of the stoma of the patient, and electronically recording the information relating to the stoma measurements for printing the customized pattern on the label having the adhesive backing in order to adapt the appliance to the patient.

According to a further embodiment, the present invention is directed to a customized ostomy appliance comprising an adhesive wafer for adhering to the stomal area of a specific patient having a stoma, the wafer having an opening for accommodating the stoma; an ostomy collection bag; a customized printed pattern indicating a cutting line for adapting the opening of the wafer to the specific patient; and a release liner having the printed pattern visible thereon for adapting the opening to the specific patient. The cutting line is obtained by measuring an outer contour of the stoma of the patient, and using the information relating to the measurements of the stoma to print the customized printed pattern for adapting the appliance to the specific patient.

The customized printed pattern may be printed on the release liner which is then placed on the adhesive wafer, or the pattern may be printed on a material having an adhesive backing for placing on the release liner.

The present invention further includes a method for customizing a standard ostomy appliance having an adhesive wafer with a hole therein for a patient having a stoma. The method includes the steps of measuring an outer contour of the stoma of the patient, recording information relating to the measurements of the stoma in electronic form, utilizing the electronic measurement information to select physical attributes of the stoma to be transferred to the ostomy appliance, and printing a customized cutting guide pattern for the hole corresponding with the selected physical attributes on a material for adhering to the wafer.

The pattern may be printed on a release liner, with the method further including the steps of placing the release liner on the wafer, and cutting the hole according to the printed pattern. Alternatively, the pattern may be printed on a label having an adhesive backing, and the method may further include the steps of placing the label on a release liner, placing the release liner on the wafer, and cutting the hole according to the pattern.

These and other objects of the invention, as well as many of the intended advantages thereof, will become more readily apparent when reference is made to the following description taken in conjunction with the accompanying drawings.

BRIEF DESCRIPTION OF THE DRAWINGS

FIG. 4 is a flow chart of a method according to the present invention: and

DETAILED DESCRIPTION OF THE INVENTION

Figure 1:
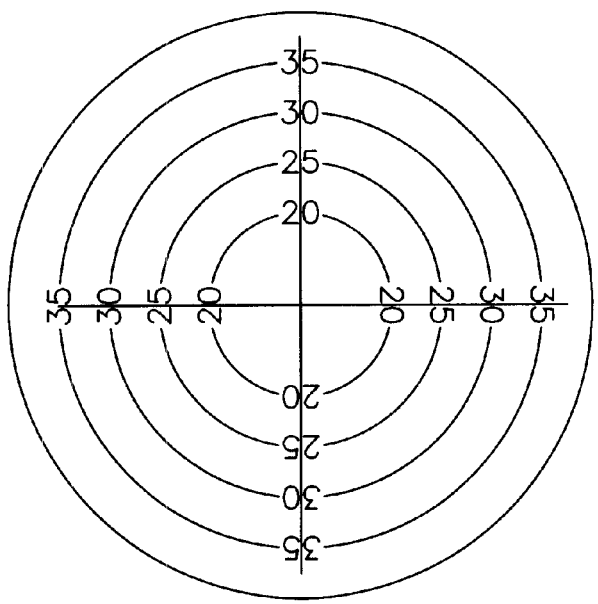
FIG. 1 shows a conventional cutting guide pattern for a release liner.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

The present invention relates to a customized ostomy appliance and a method for customizing an ostomy appliance having an adhesive wafer. The appliance is customized by measuring the outer contour of the stoma of the patient, recording the information relating to the measurements of the stoma area, transforming the recorded information into electronic form, utilizing the electronic information to select physical attributes, i.e., the measurement data, of the ostomy device to be customized and to have the physical attributes selected in accordance with the measurement information transferred to the ostomy appliance, and using the information to print a cutting guide pattern on a material for adhering to the adhesive wafer. The method offers a simple and efficient method of customizing ostomy appliances without involving substantial logistic problems with respect to producing, storing and distributing the customized products.

The information is preferably stored in electronic form together with information identifying the patient as attributes in a manner known per se and may then be used for controlling the printing of a customized cutting guide or pattern for the patient.

Figure 2:
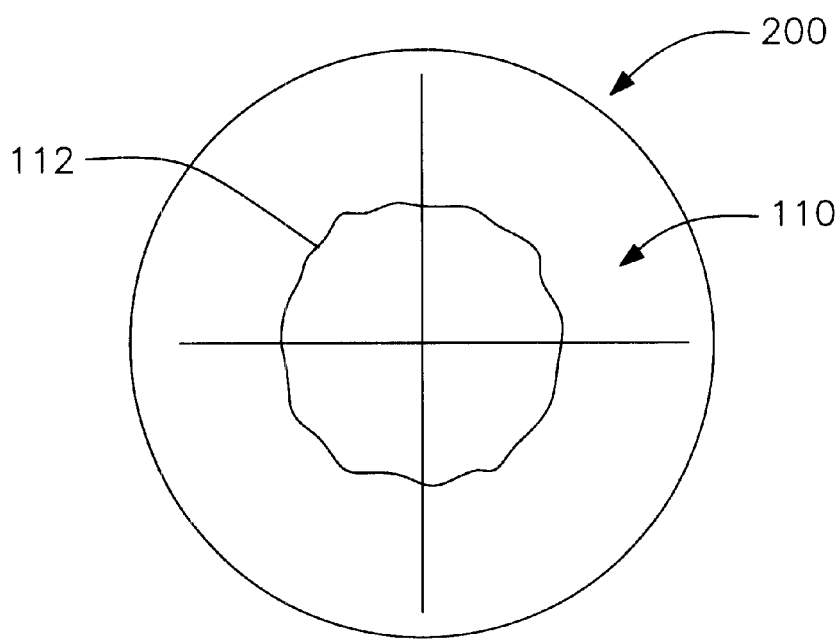
FIG. 2 shows a label according to the present invention showing a cutting line customized to the user.

The printing may be carried out in-line by printing directly on the material on a finished ostomy appliance as a last step or in an earlier separate step. A representative customized cutting guide is shown in FIG. 2, The cutting guide is embodied on a label, generally designated by the reference numeral 200, having a pattern thereon, generally designated by the reference numeral 110, which defines a cutting line 112.

Figure 3:
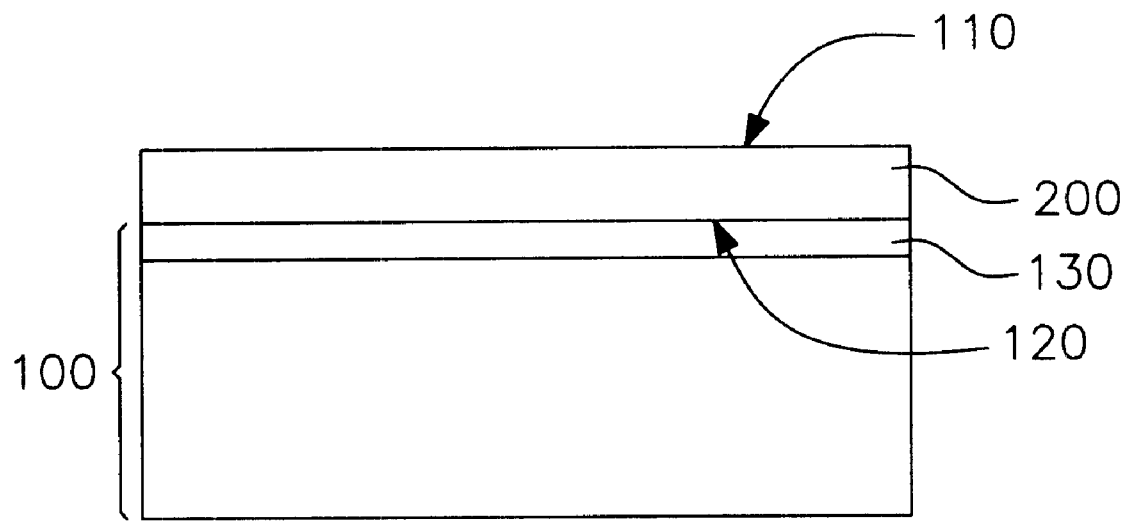
FIG. 3 is a block diagram of the components of a representative label and ostomy appliance in accordance with the present invention.

As shown in block diagram format in FIG. 3, the present invention may be embodied as a customized label 200 having a pattern 110 and an adhesive backing 120 for adhering to a release liner 130 of a standard ostomy appliance, generally designated by the reference numeral 100. As discussed above, such ostomy appliance 100 also has an adhesive wafer with a hole therein for adhering to the stomal area of a patient (not shown). The ostomy appliance 100 also optionally includes an ostomy collecting bag (not shown) attached to the adhesive wafer by an attachment means (not shown).

The customized pattern 110 on the label 200 defines a cutting line 112 corresponding to the stomal area of the patient for adapting the opening to the patient's stoma. The pattern for the cutting line is obtained by measuring an outer contour of the stoma of the patient, and electronically recording the information relating to the stoma measurements for printing the customized pattern on the label having the adhesive backing in order to adapt the appliance to the patient.

In use, the printed cutting guide is placed on the adhesive wafer or the release liner and the hole of the wafer is adapted to the periphery of the stoma of the specific patient. Such cutting may be performed by the patient or by the person in charge of delivering the ostomy appliances to the patient, typically a nurse or other assistant persons, e.g., in the patient's home, in a clinic or in a hospital. It is also foreseen that the cutting may be performed by a manufacturer or distributor who is then able to deliver customized products directly to the users by mail.

As summarized in FIG. 4, the present invention includes a method for customizing an ostomy appliance including an adhesive wafer and optionally a collection bag. The method comprises the steps of measuring the outer contour of the stoma of the patient, step 10, recording the information relating to the measurements of the stoma area, step 20, transforming the recorded information into electronic form, step 30, utilizing the electronic information to select physical attributes of the ostomy device, step 40. printing a cutting guide pattern on a material for adhering to the adhesive wafer, step 50, applying the cutting guide, step 60, and cutting the hole to customize the appliance, step 70.

Figure 5:
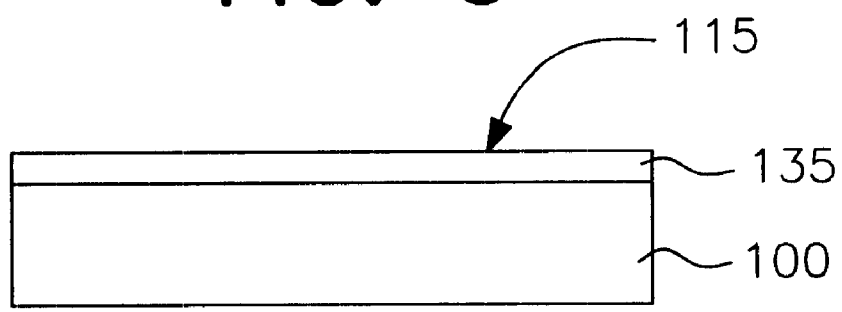
FIG. 5 is a block diagram of the components of another embodiment in accordance with the present invention.

In one embodiment of the present invention shown in the block diagram of FIG. 5, the pattern 115 is printed on a release liner 135 for placing on the adhesive layer of appliance 100 which enables simple production of one or more series of customized ostomy appliances.

In another preferred embodiment shown in block diagram format in FIG. 3, the label 200 includes a pattern 110 printed on a material having an adhesive backing 120 for placing on the release liner 130 of the appliance 100 which enables customizing of the ostomy appliance just before delivery which results in cost saving with respect to transportation and storing of customized ostomy appliances. The pattern is typically delivered in the form of a number of adhesive labels enabling an easy and simple customization of a standard product.

In a further aspect, the invention relates to a release liner having a customized printed cutting guide pattern corresponding to the stoma of a patient. The pattern defining the cutting line may be obtained by recording the information relating to the measurements of the stoma of the patient, transforming the recorded information into electronic form, optionally storing the data and utilizing the electronic information to select physical attributes of the ostomy device and have physical attributes selected in accordance with the measurement information transferred to the release liner, thereby utilizing the measurement information for printing the cutting guide pattern on a material for covering the adhesive wafer.

In a still further and preferred aspect, the invention relates to a label having an adhesive for adhering to the release liner of an ostomy appliance having a stoma receiving opening, the label comprising a customized printed cutting guide pattern corresponding to the stomal area of a patient. The customized pattern defining the cutting line may be obtained by recording the information relating to the measurements of the stoma of the patient, transforming the recorded information into electronic form, optionally storing the data and utilizing the electronic information to select physical attributes of the ostomy device and have physical attributes selected in accordance with the measurement information transferred to an adhesive label, thereby utilizing the measurement information for printing the pattern on a material having an adhesive backing.

The invention furthermore relates to a customized ostomy appliance including an adhesive wafer having a stoma receiving opening, attachment means for attaching an ostomy collection bag and a customized printed pattern indicating the cutting line for adapting the appliance to the specific ostomate. The customized pattern defining the cutting line is defined after measuring the outer contour of the stoma of the patient, recording the information relating to the measurements of the stoma, transforming the recorded information into electronic form, optionally storing the data and utilizing the electronic information to select physical attributes of the ostomy device and have physical attributes selected in accordance with the measurement information transferred to the ostomy appliance, such that the electronic measurement information is utilized for printing the pattern on a material for covering the adhesive wafer.

In a still further embodiment, the invention relates to a customized ostomy appliance including an adhesive wafer having a stoma receiving opening and an ostomy collection bag and a customized printed pattern indicating the cutting line for adapting the appliance to the specific ostomate. The cutting line is defined by measuring the outer contour of the stoma of the patient, recording the information relating to the measurements of the stoma, transforming the recorded information into electronic form, optionally storing the data and utilizing the electronic information to select physical attributes of the ostomy device and have physical attributes selected in accordance with the measurement information transferred to the ostomy appliance, such that the electronic measurement information is utilized for printing the pattern on a material for covering the adhesive wafer.

The adhesive wafer of an ostomy appliance may be made from any appropriate skin friendly material known per se for the purpose and may also comprise a top film known per se. The skin-friendly adhesive may be any skin-friendly adhesive known per se, e.g., an adhesive comprising hydrocolloids or other moisture absorbing constituents for prolonging the time of use. The adhesive may suitably be of the type disclosed in GB patent specifications Nos. 1 280 631 and 1,586,182, in EP Published Applications Nos. 0 097 846, 0 264 299, 0 272 149 and 0 415 183, in WO Publication No. 88/06894, and in U.S. Pat. Nos. 3,419,006, 3,972,328, 4,538,603 and 4,867,748. Especially preferred are the adhesives disclosed in U.S. Pat. Nos. 4,367,732, 5,051,259 and 5,714,225.

The attachment means for attaching an ostomy collection bag may be a system known per se comprising matching coupling rings or matching flanges and adhesive surfaces.

A release liner may for instance be siliconized paper. It does not need to have the same contour as the dressing, e.g., a number of dressings may be attached to a larger sheet of protective cover. The protective cover is not present during the use of the dressing of the invention and is therefore not an essential part of the invention.

A label may be prepared from any appropriate material which may be provided with a suitable adhesive for adhering the label to the release liner and holding it in place when cutting along the cutting guide as long as the materials are compatible and the adhesive has no adverse effect on the ostomy appliance.

The printing of the cutting line may be carried out using any suitable manner known per se for printing on the material in question.

A collection bag may be any suitable conventional collection bag known per se.

The foregoing descriptions and drawings should be considered as illustrative only of the principles of the invention. The invention may be configured in a variety of shapes and sizes and is not limited by the dimensions of the preferred embodiment. Numerous applications of the present invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

What is claimed is:

1. A customized label having an adhesive backing for adhering to a release liner of an ostomy appliance having an adhesive wafer for adhering to a stomal area of a patient with a stoma, said wafer including an opening for accommodating said stoma, said label comprising a customized pattern defining a cutting line corresponding to the stomal area of the patient for adapting the opening of said wafer to said patient's stoma, said pattern for said cutting line being obtained by measuring an outer contour of the stoma of the patient, and electronically recording the information relating to the measurement of the stoma for printing the customized pattern on the label having the adhesive backing in order to adapt the appliance to said patient.

2. A customized ostomy appliance comprising an adhesive wafer for adhering to a stomal area of a specific patient with a stoma, said wafer having an opening for accommodating said stoma, an ostomy collection bag, a customized printed pattern indicating a cutting line for adapting the opening of said wafer to the specific patient, and a release liner having said printed pattern visible thereon placed on said wafer for adapting the opening to the specific patient, said cutting line being obtained by measuring an outer contour of the stoma of the patient, and using the information relating to the measurement of the stoma to print said customized printed pattern for adapting the appliance to the specific patient.

3. The ostomy appliance as claimed in claim 2, wherein the customized printed pattern is printed on the release liner.

4. The ostomy appliance as claimed in claim 2, wherein the customized printed pattern is printed on a material having an adhesive backing placed on the release liner.

5. The ostomy appliance as claimed in claim 2, further comprising a body side member including said wafer and attachment means for attaching said ostomy collection bag to said body side member.

6. The ostomy appliance as claimed in claim 2, wherein said information relating to the measurement of the stoma is used to print said customized printed pattern by recording the measured information, transforming the recorded information into electronic information, and using the electronic information to select physical attributes of the ostomy appliance in accordance with the measurement information to generate said customized printed pattern for printing onto material adhered to the adhesive wafer.

7. The ostomy appliance as claimed in claim 6, wherein the material is the release liner.

8. The ostomy appliance as claimed in claim 6, wherein the material is a material having an adhesive backing which is placed on the release liner.

9. A method for customizing a standard ostomy appliance including an adhesive wafer with a hole therein for a patient having a stoma comprising the steps of:

measuring an outer contour of the stoma of the patient;

recording information relating to the measurement of said stoma in electronic form;

utilizing the electronic measurement information to select physical attributes of the stoma to be transferred to the ostomy appliance; and printing a customized cutting guide pattern for the water hole corresponding with the selected physical attributes on a material for adhering to said wafer.

10. The method for making a customized ostomy appliance as set forth in claim 9, wherein the material is a release liner, and further comprising the steps of placing the release liner on said wafer, and cutting the hole according to said pattern.

11. The method for making a customized ostomy appliance as set forth in claim 9, wherein the material is a label having an adhesive backing, and further comprising the steps of placing the label on a release liner placed on said wafer, and cutting the hole according to said pattern.

* * * * *